United States Patent
Brill et al.

[11] Patent Number: 5,356,933
[45] Date of Patent: Oct. 18, 1994

[54] ANTIFUNGAL COMPOUNDS

[75] Inventors: Gregory M. Brill, Wildwood; James B. McAlpine, Libertyville, both of Ill.; Ronald R. Rasmussen, Burlington, Wis.

[73] Assignee: Abbott Laboratories, Abbott Park, Ill.

[21] Appl. No.: 84,335

[22] Filed: Jun. 28, 1993

Related U.S. Application Data

[63] Continuation of Ser. No. 874,671, Apr. 27, 1992, abandoned.

[51] Int. Cl.$^5$ .................... A01N 37/06; C07C 61/22
[52] U.S. Cl. .................... 514/548; 549/389; 554/121
[58] Field of Search .................... 554/121; 514/548

[56] References Cited

U.S. PATENT DOCUMENTS

| | | | |
|---|---|---|---|
| 5,151,365 | 9/1992 | Dombrowski et al. | 435/254 |
| 5,166,217 | 11/1992 | Bartizal et al. | 514/455 |
| 5,182,298 | 1/1993 | Helms et al. | 514/455 |

*Primary Examiner*—Nicky Chan
*Attorney, Agent, or Firm*—Andreas M. Danckers

[57] ABSTRACT

Novel compounds having the structural formula

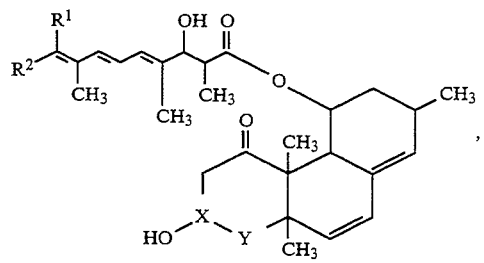

and pharmaceutically acceptable salts and prodrugs thereof, wherein one of $R^1$ and $R^2$ is hydrogen and the other is —CH=CHCOOH, X is >CH—, and Y is —O—; or, alternatively, the bond between X and Y is not present, X is —CH$_2$—, and Y is —OH, as well as methods for their use, pharmaceutical compositions containing the same, and a process for their preparation via fermentation.

5 Claims, 4 Drawing Sheets

ANTIFUNGAL COMPOUNDS

This application is a continuation of Ser. No. 874,671, filed Apr. 27, 1992, now abandoned.

TECHNICAL FIELD

The present invention relates to novel compounds and compositions thereof which have biological activity as antifungal agents, especially against *Candida albicans*. More particularly, the invention relates to polycyclic compounds named "calbistrins", as well as to a method for treating fungal infections and a process for producing such compounds by fermentation.

BACKGROUND OF THE INVENTION

Current drugs used in the treatment of systemic fungal infections include polyenes, azoles and nucleoside drugs which have deleterious side effects due to their cytotoxicity. Compounds which possess a narrow spectrum of target organisms are advantageous in some cases, especially when the potential for cytotoxicity in the host is reduced.

McGahren et al. have reported an unusual fungal metabolite, LL-N313ζ, which contains a hydroxylated fused ring system similar to certain of the compounds of the present invention (*J. Amer. Chem. Soc.*, 96:1616–77 (1974)). However, the reported compound is believed to lack the tetraene diacid half-ester possessed by the calbistrins disclosed herein, and has other structural differences at what would be C-13 of these compounds. Also, LL-N313ζ is reportedly inactive as an antimicrobial agent (McGahren et al., *J. Org. Chem.* 41:66–71 (1976)).

SUMMARY OF THE INVENTION

In one aspect of the present invention are disclosed antifungal compounds having the following structural formula (I):

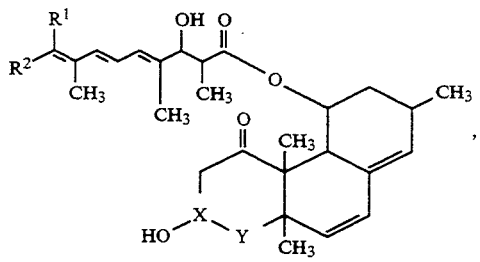

and pharmaceutically acceptable salts and prodrugs thereof, wherein one of $R^1$ and $R^2$ is hydrogen and the other is —CH=CHCOOH; X is >CH—; and Y is —O—; or, alternatively, the bond between X and Y is not present; X is —CH$_2$— and Y is —OH.

The above compounds are found to be particularly effective against *Candida albicans*. Accordingly, in a second aspect of the present invention is disclosed a method for the treatment of Candida and other fungal infections, comprising the administration to a patient in need of a therapeutically effective amount of a compound of formula (I).

In a further aspect of the present invention, a process for the preparation of the compounds of formula (I) is disclosed, comprising the fermentation of a suitable fungal species of the genus Penicillium. Useful in such a method is a related aspect of the present invention, namely, a biologically pure culture of a microorganism capable of producing a compound of the invention. Preferably, the microorganism in the above process and pure culture is the fungal strain *Penicillium restrictum* strain AB 1875C-28.

In yet another aspect of the invention are disclosed pharmaceutical compositions useful in the treatment of fungal infections, comprising a compound of formula (I) in combination with a pharmaceutically-acceptable carrier or diluent.

BRIEF DESCRIPTION OF THE DRAWINGS

The compounds of the present invention will be described in connection with the appended drawings, in which.

DETAILED DESCRIPTION OF THE INVENTION

Figure 1:
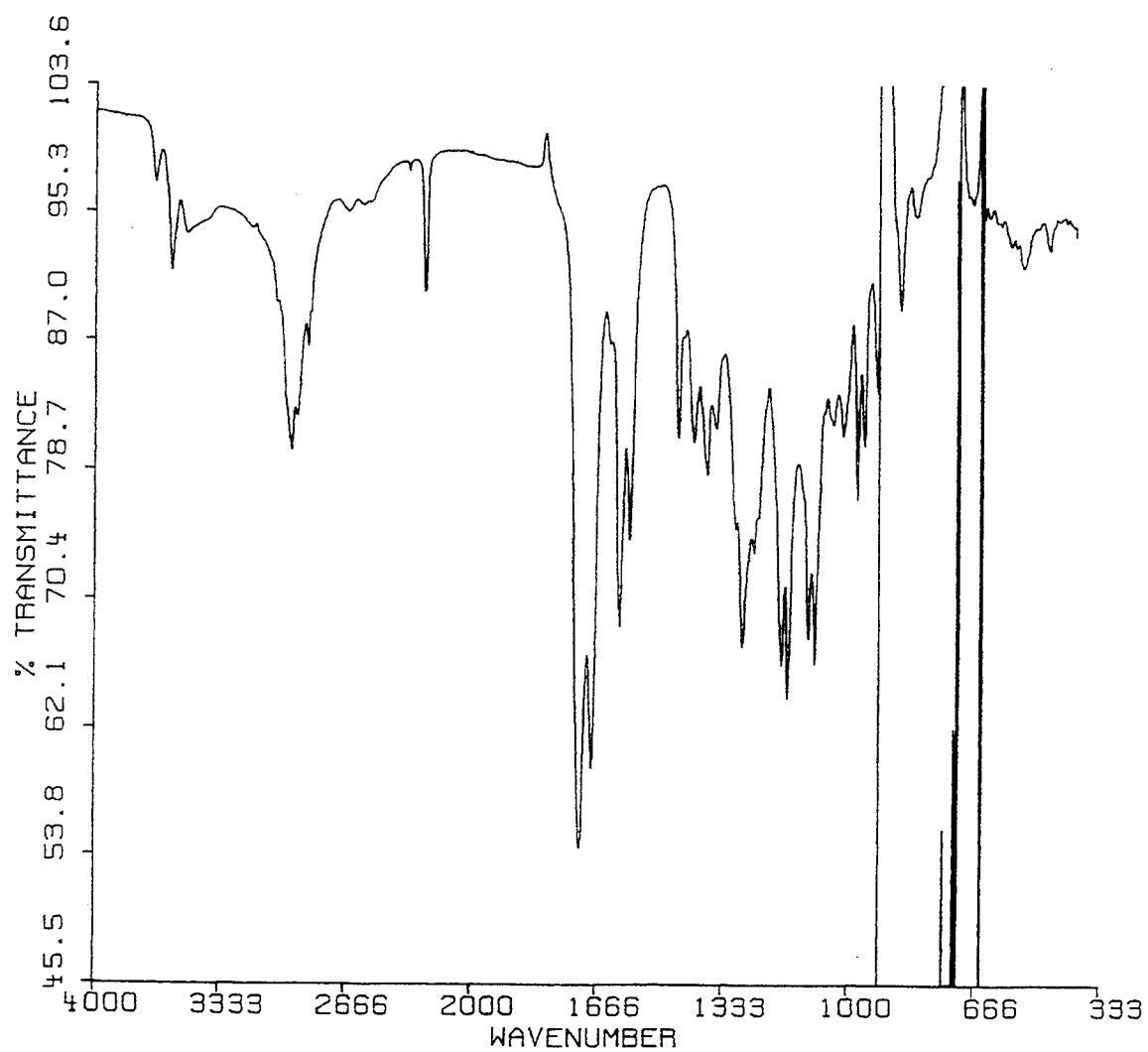
FIG. 1 is an infrared (IR) absorption spectrum of Calbistrin A.

The present invention comprises compounds having the structural formula (I) shown above. Given the generic name calbistrins, these compounds include the following four species:

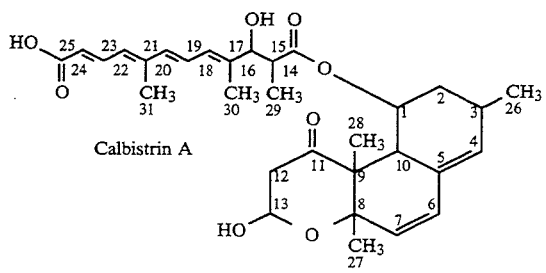

Calbistrin A

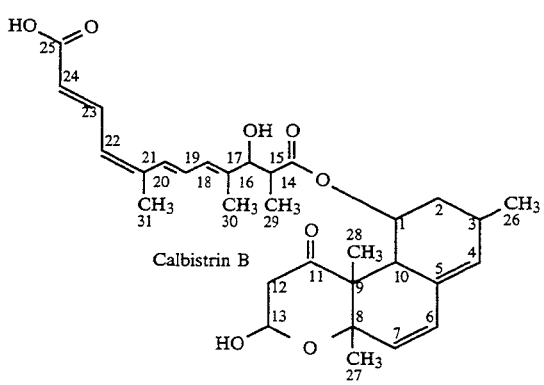

Calbistrin B

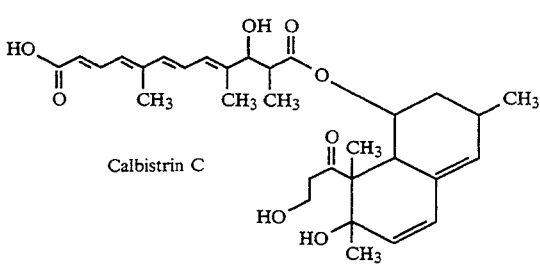

Calbistrin C and

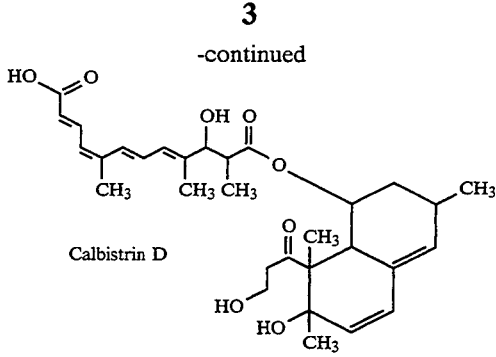

Calbistrin D

Of these, calbistrins A and B are preferred embodiments of the compounds of the invention, and calbistrin A is especially preferred.

The compounds of the present invention also include pharmaceutically acceptable salts and prodrugs of the above calbistrins. By "pharmaceutically acceptable salts" is meant those salts which are, within the scope of sound medical judgment, suitable for use in contact with the tissues of humans and lower animals without undue toxicity, irritation, allergic response and the like, commensurate with a reasonable risk-to-benefit ratio, and effective for their intended use in the chemotherapy and prophylaxis of antimicrobial infections.

Pharmaceutically acceptable salts are well known in the art. For example, S. M. Berge et al. describe pharmaceutically acceptable salts in detail in *J. Pharmaceutical Sciences*, 66:1–19 (1977), incorporated herein by reference. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, alginate, cyclopentanepropionate, digluconate, dodecylsulfate, ethanesulfonate, hemisulfate, heptanoate, hexanoate, 2-naphthalenesulfonate, pamoate, persulfate, pivalate, propionate, undecanoate salts and the like, and they may be prepared according to conventional methods. Representative alkali or alkaline earth metal salts include sodium, calcium, potassium, magnesium salts and the like. Further pharmaceutically acceptable salts include, when appropriate, quaternary ammonium salt compounds formed using counter-ions such as halide, hydroxide, carboxylate, sulfate, phosphate, nitrate, loweralkyl sulfonate and arylsulfonate.

The term "prodrugs" as used herein refers to compounds that are rapidly transformed in vivo to yield the parent compounds of formula (I), as for example by hydrolysis in blood. T. Higuchi and V. Stella provide a thorough discussion of the prodrug concept in "Prodrugs as Novel Delivery Systems", *A.C.S. Symposium Series*, Vol. 14, American Chemical Society (1975), incorporated herein by reference. Ester derivatives may be useful as prodrugs of compounds containing carboxyl groups, and can be found on pages 14–21 of "Bioreversible Carriers in Drug Design: Theory and Application", ed. E. B. Roche, Pergamon Press (1987), also incorporated herein by reference. Examples of prodrug-forming ester groups include pivaloyloxymethyl, acetoxymethyl, phthalidyl, indanyl and methoxymethyl, as well as other such groups known in the art.

The pharmaceutical compositions of the present invention comprise a therapeutically effective amount of one or more of the compounds of the invention formulated together with one or more pharmaceutically acceptable carriers. As used herein, "pharmaceutically acceptable carrier" means a non-toxic solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops including opthalmic formulations), buccally, or as an oral or nasal spray.

By a "therapeutically effective amount" of the compound of the invention is meant a sufficient amount of the compound to treat fungal infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the pathogen being treated and the severity of the infection; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of a compound of the invention administered to a human or other mammal in single or in divided doses can be in amounts, for example, from 0.05 to 50 mg/kg body weight or more usually from 0.2 to 2 mg/kg body weight. Single dose compositions may contain such amounts or submultiples thereof to make up the daily dose. In general, treatment regimens according to the present invention comprise administration to a patient in need of such treatment from about 10 mg to about 100 mg of the compound(s) of this invention per day in multiple doses or in a single dose of from 10 mg to 30 mg.

The present invention also comprises a preparative process, according to which the compounds of the invention are obtained by fermentation These compounds may be produced by culturing microorganisms of the genus Penicillium which are capable of producing the calbistrin compounds in an appropriate medium. One such microorganism is a novel variant of the fungus *Penicillium restrictum*, designated *Penicillium restrictum* strain AB 1875C-28, which was isolated from a soil sample collected in Brazil. A culture of *Penicillium restrictum* strain AB 1875C-28 has been deposited under the terms of the Budapest Treaty with the National Center for Agricultural Utilization Research, United States Department of Agriculture, 1815 North University Street, Peoria, Ill., 61604, U.S.A., and has been accorded the accession number NRRL 18926.

Although other culture methods are feasible, a liquid, submerged, agitated culture process is preferred. Media which are useful include an assimilable source of carbon such as starch, sugar, molasses, glycerol, a combination of glucose plus molasses, etc.; an assimilable source of nitrogen such as protein, protein hydrolysate, polypeptides, amino acids, peptone plus yeast extract or whole yeast, etc.; and other organic and inorganic ingredients which can be added to stimulate production of the calbistrins such as inorganic anions and cations including potassium, magnesium, calcium, ammonium, sulfate, carbonate, phosphate and chloride. Further, buffers such as calcium carbonate can be added to aid in controlling the pH of the fermentation medium.

Aeration can be provided by forcing sterile air through the fermentation medium. Cultures may also be agitated by shaking the container or by stirring the culture, as for example with a mechanical stirrer.

The fermentation is generally carried out in a temperature range of from about 18° C. to about 35° C. The pH of the fermentation is preferably maintained between pH 3 and pH 9. The compounds are produced and accumulated between 3 and 14 days after inoculation of the fermentation medium.

The compounds of the present invention may be isolated from the fermentation beer by a series of concentration procedures. An initial extract of the wet mycelia is made with acetone or a similar water-miscible agent suitable for extracting organic materials from fungal tissue. The initial extract is concentrated to a substantially aqueous residue. At this point the residue is extracted with an organic solvent, such as ethyl acetate, which is again concentrated.

The active material obtained by the larger scale extractions is then purified by a series of chromatographic partitions, utilizing a droplet counter-current (DCC) device. It may be necessary to repeat the purification with different mixtures of solvent, which may be varied as appropriate by those skilled in the art, in order to achieve the necessary degree of separation of the active compounds. In some cases a final preparative HPLC purification step may be used.

Biological activities of the extracts and of the various fractions may be monitored by use of disc diffusion bioassays on agar plates seeded with an appropriate target organism, such as *Candida albicans*. The activity of the compounds of the present invention in general may then be tested against a variety of fungi using standard assay procedures. Minimum inhibitory concentrations (MICs) are determined by, for example, the broth dilution method as described in detail in Example 9 below.

The foregoing will be better understood by reference to the following examples, which are provided for purposes of illustration and art not intended as a limitation of the invention.

EXAMPLE 1

Characterization of the Microorganism

Cultures of *Penicillium restrictum* strain AB 1875C-28 were prepared and characterized using the procedures of Pitt (*The Genus Penicillium and its Teleomorphic states, Eupenicillium and Talaromyces*, Academic Press, London, 1979). Tap water agar was included in the study since reproductive structures were not observed on the recommended media. The morphological and cultural characteristics of strain AB 1875C-28 on four media are described below. Observations were made after 7 days incubation at 25° C. unless otherwise indicated.

Czapek yeast extract agar

Colonies white, floccose, raised, sulcate, 20–23 mm diam. with a clear pale yellow exudate. Margins sunken, distinct and smooth with slight medium buckling. Reverse pale yellow, no soluble pigments. At 37° C., colonies white, floccose, strongly sulcate and convoluted, often raising the colony off the agar surface, 12–15 mm diam. with a clear pale yellow exudate. Margins distinct and smooth, no soluble pigments. Penicilli not found at either temperature. No germination at 5° C.

Blakeslee's malt extract agar

Colonies white, floccose to umbonate, raised, 17–20 mm diam., no exudate. Margins distinct, fimbriate; reverse pale yellow, no soluble pigments. Penicilli not found.

25% Glycerol nitrate agar

Colonies white, raised, floccose and sulcate, 14–17 mm diam., no exudate. Margins distinct, sunken and smooth; reverse clear pale yellow to light yellow brown, no soluble pigments. No reproductive structures found.

Tap water agar

Colonies white, mycelium floccose, appressed and very limited, 2–4 mm diam., no exudate. Margins fimbriate. Stipes borne on substrate mycelium, smooth and short, 12.5–17 $\mu m \times 2.5$–2.8 $\mu m$. Penicilli nonvesiculate, strictly monoverticillate; phialides 1–4 per verticil, terminal to subterminal, ampulliform, primarily short, 5–7.5 $\mu m \times 2.5$–2.8 $\mu m$, up to 7 $\mu m$ when long collula formed, some producing a distinct collar near terminus. Conidia spheroidal to ellipsoidal, 3–3.5 $\mu m \times 3$–3.2 $\mu m$ bearing longitudinal ridges and prominent disjunctors.

EXAMPLE 2

30L Fermentation

*Penicillium restrictum* AB 1875C-28 was maintained as a frozen inoculum stock by freezing a portion of the original inoculum and storing it at −70° C. One medium (Table 1) was used for seed growth and another medium (Table 2) was used for fermentation.

Seed flasks were prepared by dispensing 600 mL of the seed medium into 2-liter Erlenmeyer flasks, which were then sterilized for 35 minutes at 121° C. and 15 psi. The seed flasks were inoculated with 2.5 mL of the frozen inoculum stock and incubated for 72 hours at 28° C. on a rotary shaker, operated at 225 rpm with a stroke of 5 cm.

Thirty liters of production medium (Table 2) were prepared in a 42 L stainless steel stirred fermentor (LH Fermentation). The medium was sterilized in the fermentor at 121° C. and 15 psi for 1 hour. Antifoaming agent XFO-371 (Ivanhoe Chemical Co., Mundelein, Ill.) was added initially at 0.01% and later as needed. The fermentor was inoculated with 1.5 L of the seed flask growth. The temperature was controlled at 22° C. The agitation rate was 250 rpm and the air flow was 0.7 vol/vol/min. The head pressure was maintained at 5 psi. The fermentation was terminated on the seventh day, with a harvest volume of 28 liters.

TABLE 1

| Ingredients | grams/liter |
|---|---|
| Seed medium | |
| Corn steep powder (Roquette Corp., Gurnee, IL) | 2.5 |

TABLE 1-continued

| Ingredients | grams/liter |
|---|---|
| Glucose monohydrate | 10.0 |
| Oat flour | 10.0 |
| (National Oats Co., Cedar Rapids, IA) | |
| Tomato paste | 40.0 |
| (Contadina Foods, Inc., Los Angeles, CA) | |
| $CaCl_2.2H_2O$ | 10.0 |
| Trace element solution | 10 mL/L |
| Distilled water to 1 liter. (The pH was adjusted to pH 6.8 with 10 N NaOH. | |
| Trace element solution | |
| $FeSO_4.7H_2O$ | 1.0 |
| $MnCl_2.4H_2O$ | 1.0 |
| $CuCl_2.2H_2O$ | 0.025 |
| $CaCl_2.2H_2O$ | 0.1 |
| $H_3BO_3$ | 0.56 |
| $(NH_4)_6MoO_2.4H_2O$ | 0.019 |
| $ZnSO_4.7H_2O$ | 0.2 |
| Distilled water to 1 liter. | |

TABLE 2

| Production Medium | |
|---|---|
| Ingredient | grams/liter |
| Glycerol | 15.0 |
| Molasses | 15.0 |
| (Chicago Sweetners, Hillside, IL) | |
| Peptone | 6.0 |
| (Difco Laboratories, Detroit, MI) | |
| NaCl | 30.0 |
| $KH_2PO_4$ | 0.6 |
| $MgSO_4.7H_2O$ | 5.0 |
| $CuSO_4.5H_2O$ | 0.001 |
| $FeSO_4.7H_2O$ | 0.003 |
| Yeast extract | 1.5 |
| Distilled water to 1 liter. (The pH was 5.5 after sterilization.) | |

EXAMPLE 3

80L Fermentation

*Penicillium restrictum* AB 1875C-28 was fermented in a 150 L New Brunswick fermentor containing 80 L of the production medium (Table 2). The fermentor was sterilized at 121° C. and 15 psi for 1 hour. Inoculum preparation was as described in Example 1, and 4L of seed flask growth was used to inoculate the fermentor. As in Example 1, antifoaming agent (XFO-371) was added at 0.01% initially and then as needed. The temperature was controlled at 22° C. The agitation rate was 200 rpm, the air flow 0.7 vol/vol/minute, and head pressure maintained at 5 psi. Seventy-two liters of fermentation broth were harvested on the seventh day.

EXAMPLE 4

100L Fermentation

A 150 L New Brunswick fermentor containing 100 liters of the fermentation medium (Table 2) was sterilized for 1 hour at 121° C. and 15 psi. Preparation of *Penicillium restrictum* AB 1875C-28 for inoculum was as described in Example 1, and 5 L of seed flask growth was inoculated into the fermentor. During fermention the temperature was controlled at 22° C. The agitation rate was 200 rpm, the air flow 0.7 vol/vol/min, and the head pressure 5 psi. Antifoaming agent (XFO-371) was used as before. The culture was harvested on the seventh day.

EXAMPLE 5

Isolation of Calbistrins A and B

Twenty-eight liters of whole beer from the fermentation of Example 2 was filtered through DICALITE® diatomaceous earth (filter aid), and the filter cake dispersed and soaked in 10 L of acetone for 20 hours. After additional stirring the mixture was filtered through glass wool-impregnated paper, and the filter cake washed with an additional 6 L of acetone. The acetone extract was concentrated on a circulating flash evaporator until approximately three liters of an aqueous acetone extract remained. This was concentrated further on a rotary evaporator, after which the aqueous residue was freeze dried. The freeze dried material was triturated with ethyl acetate and then methanol (three times with 300 mL portions of each solvent). The solvents were combined and concentrated under reduced pressure. This concentrate was chromatographed in the solvent system $MeOH:H_2O:CHCl_3:CCl_4$ (5:2:3:2 and again in 5:2:1:4) using a droplet counter-current (DCC) device with the lower phase as the stationary phase. This device (made in-house) consists of 100 loops of teflon tubing with an approximate stationary phase retention volume of 450 mL, of which approx. 90–95% is retained during use. The coil has a mobile phase volume of approximately 70 mL. The DCC was run at a rate of 1–1.5 mL/minute, and fractions of 8–10 mL were collected.

Activity was found in fractions 132–164 (334 mg), which were combined and concentrated. The concentrate was then chromatographed in the solvent system $MeOH:50$ mM $KH_2PO_4:CHCl_3:CCl_4$ (10:4:5:5) using the DCC device with the lower phase as the stationary phase. The flow was 1–1.5 mL/min, with fractions of 8–10 mL being collected. The load sample was chromatographed in two runs. This yielded two active bands from each run: In the first run, fractions 64–76 (34 mg) and 77–86 (26 mg); and in the second run, fractions 58–70 (43 mg) and 71–82 (64 mg).

The first active band from the second run (fractions 58–70) was chromatographed on a PARTISIL® 10 ODS-3 (C-18) semi-preparative HPLC column (Whatman Co.) in the solvent system MeOH:50 mM $NH_4OAc$ (68:32, 5 mL/min, five runs). Activity was extracted from the mobile phase with chloroform. NMR and mass spectral studies revealed the main active peak isolated from this chromatography to be calbistrin B with a minor amount of calbistrin A. The fractions 64–76, 77–86 and 71–82 from the PDCC chromatography were combined and chromatographed on a similar column in the solvent system MeOH:50 mM $NH_4OAc$ (68:32, 5 mL/min, five runs). Two active peaks were isolated from this chromatography; calbistrin A and calbistrin B.

EXAMPLE 6

Alternate Isolation of Calbistrin A

Seventy-two liters of whole beer from Example 3 were filtered through glass wool-impregnated paper and the filter cake dispersed and soaked in 16 L of acetone for 20 hours. After additional stirring the mixture was filtered through glass wool-impregnated paper and the filter cake was washed with an addition 16 L of acetone. The acetone extract was concentrated on a circulating flash evaporator until approximately three liters of aqueous acetone was obtained, which in turn was extracted with three equal volumes of ethyl acetate. The ethyl acetate extracts were combined and concentrated to a residue which was then partitioned in the solvent system MeOH:H$_2$O:CHCl$_3$:CCl$_4$ (5:2:3:2, total volume 800 mL), the upper phase being washed with four portions of the lower. The lower layers were combined and concentrated to give an oily residue. The oily concentrate was then partitioned between methanol and n-heptane (a total of 800 mL), the methanol layer being washed with four 300-400 mL portions of the n-heptane.

The methanolic concentrate, which contained the active compounds, was chromatographed in the solvent system MeOH:50 mM KH$_2$PO$_4$ (pH=5.0):CHCl$_3$:CCl$_4$ (10:4:5:5) using the DCC device with the lower phase as the stationary phase. The flow was 1-1.5 mL/min, and fractions of approximately 8 mL were collected. The chromatography yielded 8.03 g of active material from two runs, each on half of the load sample. This active material was chromatographed in the solvent system CHCl$_3$:CCl$_4$:MeOH:50 mM KH$_2$PO$_4$ (pH 5.0) (1:4:5:2, upper phase stationary, 2 mL/min, 8-10 mL fractions) on the DCC. The major active band, fractions 67-168, yielded 2.45 g of material which was then chromatographed on silica gel 60 G (E. Merck, Darmstadt, West Germany) in the solvent system EtOAc:toluene:MeOH (90:10:10, 2.5×35 cm column) to yield 1.53 g of active material. This active material was chromatographed in the solvent system MeOH:50 mM NH$_4$OAc (pH 5.0):toluene:EtOAc (4:2:2:3,upper phase stationary, 0.5 mL/min, 5 mL fractions) on the DCC to yield 70 mg of active material from fractions 26-60.

This active material was chromatographed on the same C-18 semi-preparative HPLC column as before using the solvent system MeOH:50 mM NH$_4$OAc (68:32, 5 mL/min, four runs). NMR and mass spectral studies revealed the main active band isolated from this chromatography to be calbistrin A with a minor amount of calbistrin B.

EXAMPLE 7

Isolation of Calbistrins A, C and D

Ninety liters of whole beer from Example 4 were filtered through glass wool-impregnated paper and the filter cake dispersed and soaked in 16 L of acetone for 16 hours. After additional stirring the mixture was filtered through glass wool impregnated paper and the filter cake washed with an addition 8 L of acetone. The acetone extract was concentrated on a circulating flash evaporator until approximately 4 L of residual aqueous acetone remained. This was extracted with three equal volumes of ethyl acetate. The ethyl acetate extracts were combined and concentrated to a residue which was then partitioned in the solvent system MeOH:H$_2$O:CHCl$_3$ (5:2:5, total volume 800 mL), the upper phase being washed with four portions of the lower. The lower layers were combined and concentrated to an oily residue. The material was then partitioned between methanol and n-heptane (a total of 800 mL), the methanol layer being washed with four 300-400 mL portions of the n-heptane.

The active methanolic concentrate was chromatographed in the solvent system MeOH:50 mM NH$_4$OAc (pH 5.0):CHCl$_3$:CCl$_4$ (10:4:5:5) using the DCC with the lower phase as the stationary phase. The flow was 1-1.5 mL/min, and fractions of approximately 10-12 mL were collected (two runs). The active material (fractions 70-170 and 66-124, respectively) was rechromatographed in the solvent system CHCl$_3$:CCl$_4$:MeOH:50 mM NH$_4$OAc (pH 5.0) (3:7:10:4) on the DCC with the upper phase as the stationary phase. The flow was 1-1.5 mL/min, and fractions of approximately 10-12 mL were (two runs, active material in fractions 30-120 and 52-104.

The concentrate containing 3.24 g of a mixture of the calbistrins was purified by preparative HPLC in 500 mg aliquots dissolved in 1.8 mL CH$_3$CN. The chromatography hardware consisted of a SEPTECH ST/LAB 800 C preparative chromatograph and a PROCHROM LC 50 column containing 250 g of YMC phenyl packing (15$\mu$) packed under an axial pressure of 50 bar. The mobile phase was pumped as a binary system at a rate of 50 mL/min and consisted of a 45 minute linear gradient starting with CH$_3$CN:2% HOAc/H$_2$O (20:80) and ending with CH$_3$CN:H$_2$O (80:20). The final solvent proportions were delivered at 50 mL/min for an additional 15 minutes before re-equilibrating the column. The effluent was monitored by UV detection at 275 nm (2.56 AUFS). One major peak and three minor peaks were observed and collected as tight cuts to maximize purity. Each was reinjected on the column and recollected to obtain compounds suitable for structure elucidation and biological testing. Each 500 mg run afforded 33.7 mg of the major ($t_R$ 36.3 min) which was characterized as calbistrin A. The minor compounds from each run ($t_R$ 35.1 min, 37.0 min and 38.0 min) were characterized as calbistrin C (9.3 mg), calbistrin D (1.7 mg) and calbistrin B (12.5 mg), respectively.

EXAMPLE 8

Characterization of the Calbistrins

Figure 2:
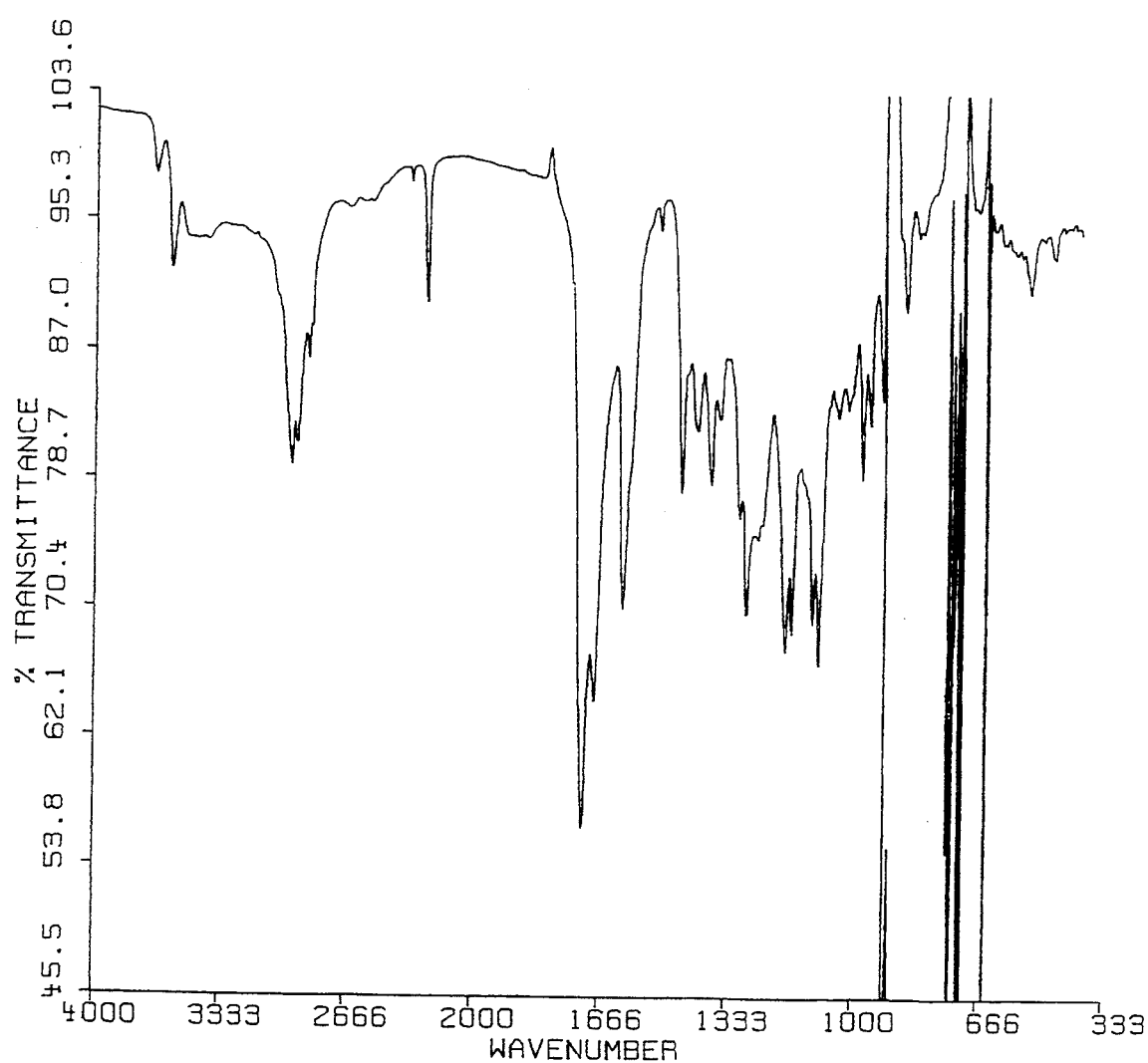
FIG. 2 is an IR absorption spectrum of Calbistrin B.
Figure 3:
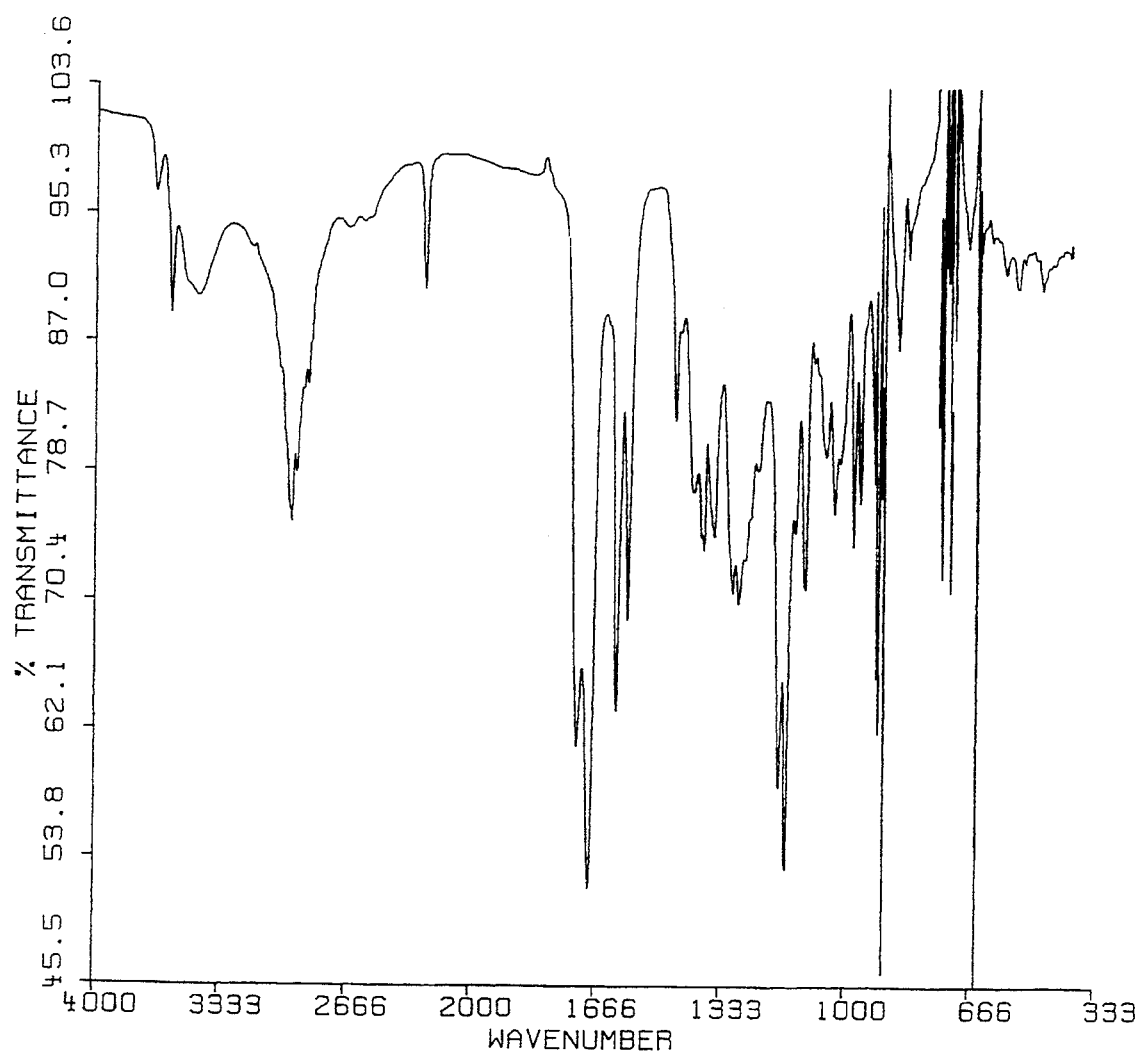
FIG. 3 is an IR absorption spectrum of Calbistrin C.
Figure 4:
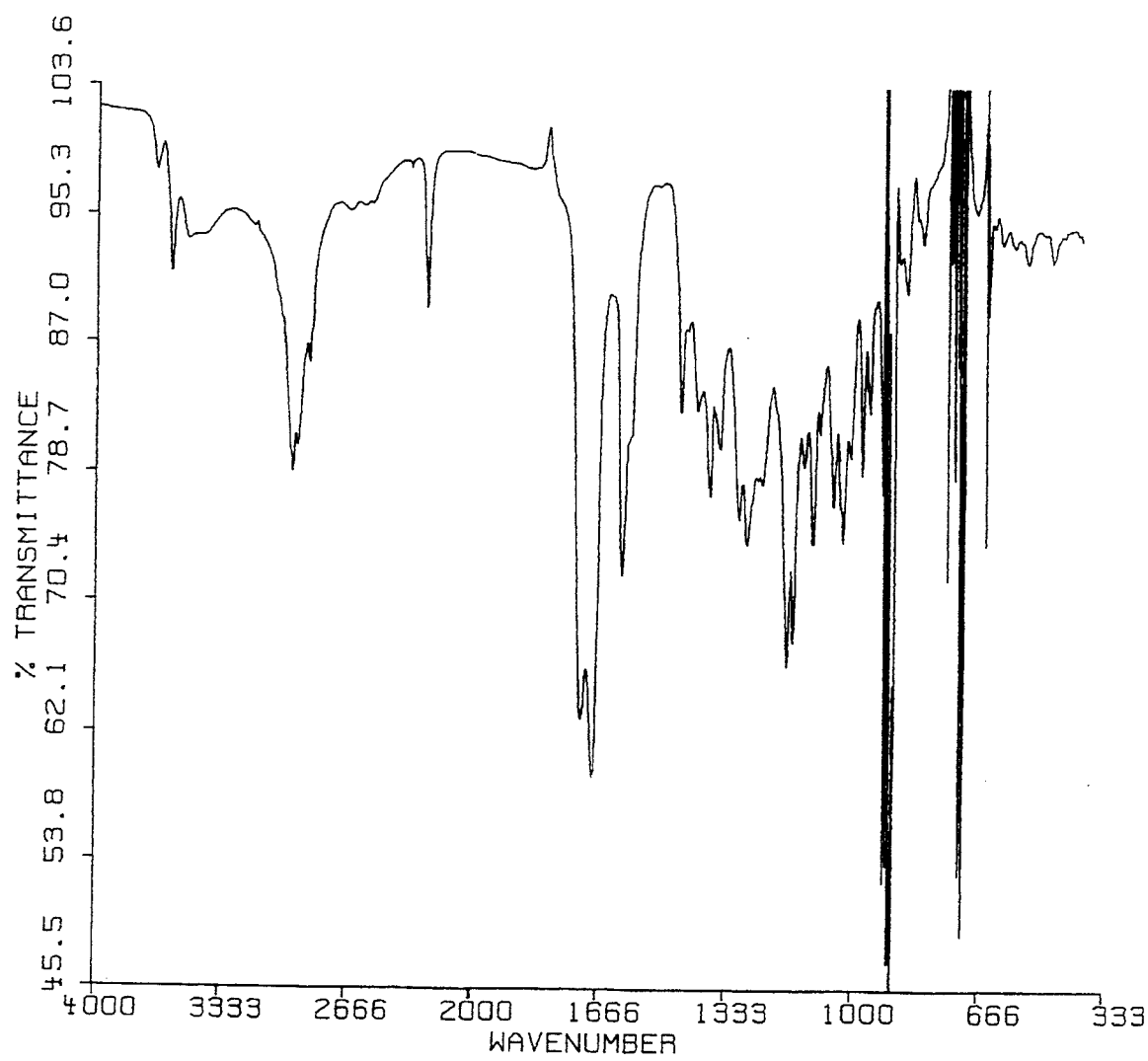
FIG. 4 is an IR absorption spectrum of Calbistrin D.

The calbistrins are soluble in common organic solvents such as dimethyl sulfoxide, methanol, acetonitrile, acetone, ethyl acetate, chloroform and benzene. High resolution fast atom bombardment (FAB) mass spectrometry in the positive ion mode gave an (M+Na)$^+$ parent mass of 563.2624 (calc. 563.2621) for calbistrin A, indicating a molecular formula of C$_{31}$H$_{40}$O$_8$. Calbistrin B gave an identical (M+Na)$^+$ parent mass of 563.2624 (calc. 563.2621 ) also indicating a molecular formula of C$_{31}$H$_{40}$O$_8$. The (M+Na)$^+$ parent mass of calbistrin C and calbistrin D were identical to each other; 565.2774 (calc. 565.2777) indicating C$_{31}$H$_{42}$O$_8$. The compounds have characteristic ultraviolet (UV) absorption spectra maxima as listed in Table 3. Each of the compounds contains an acid conjugated tetraene chromophore and a cyclic diene chromophore. Calbistrins A and B differ only at the C21-C22 double bond, with calbistrin A being the trans isomer. Likewise, calbistins C and D differ only at the C21-C22 double bond, with calbistrin C being the trans isomer. The calbistrins are characterized in $^1$H NMR and $^{13}$C NMR experiments as shown in Tables 4 and 5. The IR absorption spectra for the calbistrins is given in FIGS. 1-4.

TABLE 3

| | Ultraviolet (UV) Absorption Spectrum Maxima | | | |
|---|---|---|---|---|
| | Calbistrin A | Calbistrin B | Calbistrin C | Calbistrin D |
| Solvent | $\lambda_{max}$ (nm)/$\epsilon$ | $\lambda_{max}$ (nm)/$\epsilon$ | $\lambda_{max}$ (nm)/$\epsilon$ | $\lambda_{max}$ (nm)/$\epsilon$ |
| MeOH | 237/22,300 | 237/22,800 | 237/19,800 | 238/21,800 |
| | 331/42,500 | 330/29,400 | 329/52,400 | 331/32,600 |
| 0.1 N NaOH— | 237/24,300 | 237/23,200 | 237/20,000 | 237/22,000 |
| MeOH | 324/52,900 | 320/38,300 | 326/53,400 | 322/38,400 |

TABLE 3-continued

Ultraviolet (UV) Absorption Spectrum Maxima

| Solvent | Calbistrin A $\lambda_{max}$ (nm)/$\epsilon$ | Calbistrin B $\lambda_{max}$ (nm)/$\epsilon$ | Calbistrin C $\lambda_{max}$ (nm)/$\epsilon$ | Calbistrin D $\lambda_{max}$ (nm)/$\epsilon$ |
|---|---|---|---|---|
| 0.1 N HCl—MeOH | 237/25,700 339/42,900 | 237/22,600 338/28,700 | 237/18,600 342/47,200 | 238/21,200 338/32,300 |

TABLE 4

$^1$H NMR Chemical Shift Data$^a$

| Proton | Mult. | Calbistrin A | Calbistrin B | Calbistrin C | Calbistrin D |
|---|---|---|---|---|---|
| 1 | br. s | 6.02 | 6.03 | 5.37 | 5.37 |
| 2a | m | 2.19 | 2.21 | 2.06 | 2.07 |
| 2b | br. dd | 1.34 | 1.34 | 1.24 | 1.25 |
| 3 | m | 2.50 | 2.50 | 2.42 | 2.43 |
| 4 | s | 5.74 | 5.73 | 5.65 | 5.65 |
| 6 | d | 6.00 | 5.99 | 5.97 | 5.97 |
| 7 | d | 5.64 | 5.64 | 5.39 | 5.39 |
| 10 | d | 2.89 | 2.89 | 3.13 | 3.13 |
| 12a | — | 2.80 dd | 2.81 dd | 3.02 dt | 3.02 dt |
| 12b | — | 2.39 dd | 2.39 dd | 2.78 dt | 2.78 dt |
| 13 | dd | 5.21 | 5.21 | — | — |
| 13a | m | — | — | 3.81 | 3.81 |
| 13b | m | — | — | 3.72 | 3.72 |
| 15 | m | 2.52 | 2.53 | 2.54 | 2.54 |
| 16 | d | 4.07 | 4.11 | 4.09 | 4.12 |
| 18 | d | 6.13 | 6.19 | 6.14 | 6.22 |
| 19 | dd | 6.74 | 6.70 | 6.74 | 6.74 |
| 20 | d | 6.41 | 6.95 | 6.41 | 6.97 |
| 22 | d | 6.30 | 6.15 | 6.30 | 6.18 |
| 23 | dd | 7.70 | 7.80 | 7.70 | 7.84 |
| 24 | d | 5.89 | 5.82 | 5.89 | 5.83 |
| 26 | d | 1.04 | 1.04 | 1.02 | 1.02 |
| 27 | s | 1.24 | 1.24 | 1.12 | 1.12 |
| 28 | s | 1.33 | 1.34 | 1.40 | 1.40 |
| 29 | d | 0.89 | 0.92 | 0.89 | 0.91 |
| 30 | s | 1.77 | 1.77 | 1.78 | 1.79 |
| 31 | s | 2.04 | 2.02 | 2.04 | 2.03 |

$^a$500 MHz in CD$_3$OD at $-5.0°$ C.

TABLE 5

$^{13}$C NMR Chemical Shift Data$^a$

| Carbon Number | Calbistrin A | Calbistrin B | Calbistrin C | Calbistrin D |
|---|---|---|---|---|
| 1 | 71.1 | 71.1 | 70.9 | 70.9 |
| 2 | 36.2 | 36.2 | 36.6 | 36.6 |
| 3 | 28.2 | 28.2 | 27.5 | 27.5 |
| 4 | 136.7 | 136.7 | 134.8 | 134.9 |
| 5 | 131.6 | 131.4 | 132.4 | 132.4 |
| 6 | 129.7 | 129.9 | 129.0 | 129.1 |
| 7 | 131.6 | 131.6 | 134.4 | 134.4 |
| 8 | 78.7 | 78.7 | 75.3 | 75.3 |
| 9 | 54.8 | 54.8 | 58.2 | 58.2 |
| 10 | 41.1 | 41.1 | 42.0 | 42.1 |
| 11 | 210.9 | 210.9 | 215.3 | 215.3 |
| 12 | 48.0 | 48.0 | 45.1 | 45.1 |
| 13 | 92.5 | 92.5 | 58.4 | 58.4 |
| 14 | 176.6 | 176.6 | 176.9 | 177.0 |
| 15 | 45.7 | 45.7 | 45.6 | 45.6 |
| 16 | 81.1 | 81.0 | 81.2 | 81.2 |
| 17 | 141.2 | 141.8 | 141.2 | 141.9 |
| 18 | 129.8 | 129.8 | 129.7 | 129.8 |
| 19 | 128.5 | 129.5 | 128.6 | 129.5 |
| 20 | 137.9 | 129.7 | 137.9 | 129.6 |
| 21 | 145.5 | 144.4 | 145.5 | 144.4 |
| 22 | 129.8 | 128.2 | 129.8 | 128.2 |
| 23 | 141.9 | 140.9 | 142.0 | 140.9 |
| 24 | 122.0 | 121.2 | 121.8 | 121.2 |
| 25 | 171.0 | 171.0 | 170.8 | 171.0 |
| 26 | 21.3 | 21.4 | 21.5 | 21.5 |
| 27 | 23.5 | 23.5 | 26.5 | 26.4 |
| 28 | 18.4 | 18.4 | 14.3 | 14.3 |
| 29 | 14.9 | 14.9 | 14.9 | 14.9 |
| 30 | 11.4 | 11.5 | 11.4 | 11.4 |
| 31 | 13.1 | 21.1 | 13.1 | 21.1 |

$^a$500 MHz in CD$_3$OD at $-5.0°$ C.

EXAMPLE 9

Assay of In Vitro Antifungal Activity

The activity of the compounds of the present invention was tested against a variety of fungi using standard assay procedures. Minimum inhibitory concentrations (MICs) were determined by the broth microdilution method, described below, using Mueller-Hinton broth.

Antibiotics were dissolved in 100% methanol and diluted to 1 mg/mL concentration; further dilutions were done in broth. Dilutions were made serially into microtiter tray wells, using an automatic or semi-automatic dispenser. The growth control well did not receive any antibiotic. Amphotericin B was the standard antibiotic for control purposes. Candida albicans ATCC 10231 was the standard quality control organism.

Organisms were inoculated into the test medium and incubated overnight at 35° C. Overnight cultures were adjusted in sterile broth to 95% transmission at 530 nm and further diluted with broth to 1:50. After addition of the antibiotics, the microtiter trays were incubated at 35°–37° C. for 16–20 hours. MIC readings were made using a reflective viewer.

The resulting MICs, shown in Table 6 below, demonstrate the antifungal activity of the compounds of the present invention.

TABLE 6

In Vitro Activity (MIC, μg/ml) Against Selected Fungal Strains

| Organism | Strain | Calbistrin A | Calbistrin B | Calbistrin C |
|---|---|---|---|---|
| Candida albicans | ATCC 10231 | 0.78 (1.56)* | 3.12 (1.56) | 50 (1.56) |
| Candida albicans | 579A | 0.78 (1.56) | 3.12 (1.56) | 50 (1.56) |
| Candida albicans | CCH 442 | 0.78 (1.56) | 3.12 (1.56) | 50 (1.56) |
| Candida albicans | ATCC 38247 | nt | 0.78 (50) | nt |
| Candida albicans | ATCC 62376 | 0.78 (1.56) | 3.12 (3.12) | 50 (1.56) |
| Candida tropicalis | NRRL Y-112 | 1.56 (1.56) | 3.12 (1.56) | 50 (1.56) |
| Candida kefyr | ATCC 28838 | 25 (1.56) | 50 (3.12) | >100 (1.56) |
| Torulopsis glabrata | ATCC 15545 | 100 (1.56) | 100 (3.12) | >100 (1.56) |
| Crytococcus albidus | ATCC 34140 | >100 (1.56) | >100 (3.12) | >100 (1.56) |
| Saccharomyces cervisiae | GS1-36 | 100 (0.39) | 100 (0.78) | >100 (0.39) |
| Aspergillus niger | ATCC 16404 | >100 (3.12) | >100 (6.25) | >100 (3.12) |

†=Calbistrin B tested on a different day than calbistrins A and C.
* = MICs for Amphotericin B in parentheses It is understood that the foregoing detailed description and accompanying examples are merely illustrative and are not to be taken as limitations upon the scope of the present invention, which is defined solely by the appended claims and their equivalents. Various changes and modifications to the disclosed embodiments will be readily apparent to those skilled in the art, and may be made without departing from the spirit and scope thereof.

What is claimed is:

1. A compound selected from the group consisting of

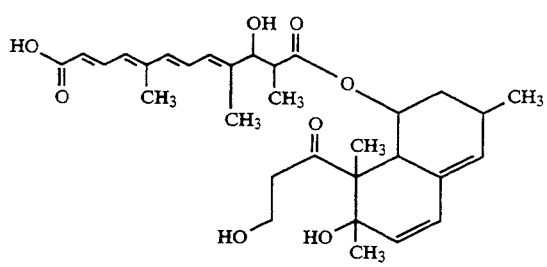

and

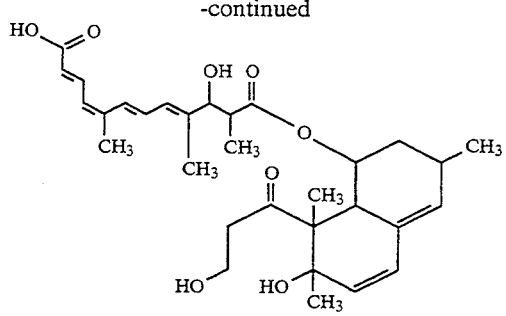

and the pharmaceutically acceptable salts and prodrugs thereof.

2. A pharmaceutical composition comprising a compound according to claim 1 in combination with pharmaceutically acceptable carrier.

3. A method for the treatment of a fungal infection, comprising administering to a patient in need a therapeutically effective amount of a compound according to claim 1.

4. A method according to claim 3, wherein the fungal infection is produced by a fungus of the genus Candida.

5. A method according to claim 4, wherein the fungus is *Candida albicans*.

* * * * *